United States Patent [19]

Girsh

[11] Patent Number: 5,064,674

[45] Date of Patent: * Nov. 12, 1991

[54] HYPOALLERGENIC MILK PRODUCTS AND PROCESS OF MAKING

[75] Inventor: Leonard S. Girsh, Melrose Park, Pa.

[73] Assignee: Immunopath Profile, Inc., Melrose Park, Pa.

[ * ] Notice: The portion of the term of this patent subsequent to Sep. 4, 2007 has been disclaimed.

[21] Appl. No.: 562,777

[22] Filed: Aug. 3, 1990

Related U.S. Application Data

[63] Continuation-in-part of Ser. No. 297,451, Jan. 13, 1989, Pat. No. 4,954,361.

[51] Int. Cl.⁵ .............................................. A23C 9/142
[52] U.S. Cl. .................................... 426/580; 426/491; 426/585; 426/801
[58] Field of Search ............... 426/491, 580, 583, 585, 426/801

[56] References Cited

U.S. PATENT DOCUMENTS

| | | | |
|---|---|---|---|
| 677,159 | 6/1901 | Meyenberg | 426/583 |
| 1,210,918 | 1/1917 | Eigelberner | 426/530 |
| 2,414,837 | 1/1947 | Riggs | 99/62 |
| 2,714,068 | 7/1955 | Bernhart et al. | 426/580 |
| 2,903,358 | 9/1959 | Block et al. | 99/54 |
| 3,003,882 | 10/1961 | Peat | 426/804 |
| 3,642,493 | 2/1972 | Arndt | 99/64 |
| 3,669,678 | 6/1972 | Kraft | 426/583 |
| 3,843,838 | 10/1974 | Arndt | 426/585 |
| 3,930,039 | 12/1975 | Kuipers | 426/583 |
| 3,978,234 | 8/1976 | Bosund et al. | 426/804 |
| 4,018,752 | 4/1977 | Buhler et al. | 426/804 |
| 4,042,575 | 8/1977 | Eustache | 426/583 |
| 4,202,909 | 5/1980 | Pederson, Jr. | 426/583 |
| 4,293,571 | 10/1981 | Olofasson et al. | 426/657 |
| 4,341,801 | 7/1982 | Weissman | 426/583 |
| 4,358,464 | 11/1982 | Soehnlen | 426/491 |
| 4,389,425 | 6/1983 | Burr, II | 426/598 |
| 4,389,426 | 6/1983 | Reissmann et al. | 426/804 |
| 4,402,938 | 9/1983 | Collins | 426/491 |
| 4,476,143 | 10/1984 | Czulak et al. | 426/804 |
| 4,518,616 | 5/1985 | Czulak | 426/583 |
| 4,528,204 | 7/1985 | Shank | 426/804 |
| 4,547,386 | 10/1985 | Chambers et al. | 426/583 |
| 4,614,653 | 9/1986 | Kakade | 426/583 |
| 4,670,268 | 6/1987 | Mahmound | 426/804 |
| 4,692,338 | 9/1987 | Irvine et al. | 426/583 |
| 4,716,120 | 12/1987 | Tsay et al. | 436/809 |
| 4,954,361 | 9/1990 | Girsh | 426/583 |

OTHER PUBLICATIONS

Sandstrom, B. et al., "Zinc Absorption From Human Milk, Cow's Milk, and Infant Formulas", Am. J. Dis. Child, vol. 137, Aug. 1983, pp. 726–729.

Theuer, R. C. et al., "Effect of Processing on Availability of Iron Salts in Liquid Infant Products, Experimental Soy Isolate Formulas", J. Agr. Food Chem., vol. 19, No. 3, May/Jun. 1971, pp. 555–558.

The Wall Street Journal, "Dairy Dilemma Milk is Found Tainted with a Range of Drugs Farmers Give Cattle", Dec. 29, 1988 at p. 1.

The Wall Street Journal, "Nestle to Sell Infant Formula Soon in the U.S.", Jun. 6, 1988.

McGilvery, R. W. et al., Biochemistry A Functional Approach, at 615 (2d ed. 1979).

The Condensed Chemical Dictionary, 203, 1095 (10th ed. 1987).

Fundamentals of Dairy Chemistry, 102–103 and 680–681, 3 ed. (N. P. Wong ed. 1988).

Primary Examiner—Marianne Cintins
Assistant Examiner—Helen Pratt
Attorney, Agent, or Firm—Seidel, Gonda, Lavorgna & Monaco

[57] ABSTRACT

A hypoallergenic milk which has the flavor and smell of natural whole mammalian milk is disclosed herein. The hypoallergenic milk is made from the ultrafiltered permeate of cow's milk, whey, or other milk fraction. The permeate is substantially free of cow's milk protein and fat. The permeate is supplemented with hypoallergenic protein, and optionally fat, vitamins and minerals to meet the minimum daily nutritional requirements for milk.

50 Claims, No Drawings

5,064,674

HYPOALLERGENIC MILK PRODUCTS AND PROCESS OF MAKING

CROSS-REFERENCE

This is a continuation-in-part of my copending patent application Ser. No. 297,451, filed Jan. 13, 1989, now U.S. Pat. No. 4,954,361 the entire disclosure of which is incorporated herein by reference.

FIELD OF THE INVENTION

A hypoallergenic milk made from the permeate of mammalian milk (i.e. the protein and fat-free component of cow's milk) is disclosed herein. The hypoallergenic milk has the flavor and smell of whole natural milk, but lacks the component which causes allergic reactions. The hypoallergenic milk has the favorable features of mother's milk, but lacks foreign animal protein, and therefore may thus be regarded as "humanized" cow's milk.

BACKGROUND OF THE INVENTION

Many persons suffer from various allergies, many of which are caused by ingesting food containing allergens.

Although the biochemistry of allergic reactions is not precisely understood, it is believed that the allergens cause, upon ingestion or other contact with the body, a specific reagin (or skin sensitizing antibody) to be formed in the bloodstream. The ability to produce reagins, chemically identified as IgE, in response to a given allergen is thought to be an inherited characteristic that differentiates an allergic person from a non-allergic person. The specificity of the allergen-reagin reaction and its dependence on molecular configuration of the allergen and reagin is similar to the antigen-antibody reaction. The degree of sensitization is dependent upon the extent of exposure to or ingestion of the allergen. In this respect, the allergen molecule, which is often a protein, may be regarded as a "key" which exactly fits the corresponding structural shape of the reagin molecule which may be likened to a "lock". When the key is inserted into the lock, an allergic reaction results.

Different materials contain different allergens. Not all persons may have the reagin with which a particular allergen can react. Therefore, some persons are not allergic to particular materials. However, when a particular reagin reacts with a specific allergen, an allergic reaction results in any number or type of symptoms. Allergic reactions range from very mild symptoms to death. For example, symptoms, both mild and severe, include skin rashes (allergic eczema and urticaria), dermal symptoms, respiratory symptoms (including allergic rhinitis and bronchial asthma), gastrointestinal symptoms, and migraine. Violent illnesses have been known to include shock-like reactions, vascular collapse and allergic anaphylaxis.

Many allergists have recognized that milk contains proteins which are allergens. The allergens of cow's milk frequently cause the formation of reagins (IgE) in many persons. Thus, many persons, including both adults and children, are allergic to cow's milk.

Milk is very frequently used in popular food products. It is used not only in cooking and baking, but it is included in hidden ways as well. For example, casein, caseinate milk solids, whey, whey solids, and lactalbumin are milk products which are components of cookies, cheeses, chocolate (in the form of milk chocolate), ice cream, butter and may be used as flavoring for other food products, such as breakfast cereals, hot and cold beverages, and desserts. These products can also be found in gravies, breading, whole, dry or evaporated milk, yogurt, sherbet, breads, waffles, creamed vegetables, mashed potatoes, pudding, creamer or any diverse products such as hot dogs or spaghetti.

Milk products, which are marketed today as hypoallergenic milk, are neither uniformly hypoallergenic to all patients, nor made from cow's milk. For example, heat processed milk, in which albumin is denatured, is of modest benefit to only a limited number of patients. A hypoallergenic vegetable soybean milk formulation devised in China has an objectionable smell and after taste. Hypoallergenic milk produced by the acid process which imitates the stomach's digestive process by utilizing hydrochloric acid to break up proteins, e.g. casein, has an objectionable smell and taste.

Accordingly, there is a need for a hypoallergenic milk which also has the taste and smell of cow's milk.

U.S. Pat. No. 4,293,571 discloses a process for the purification of purified protein hydrolysate. In this process, an aqueous solution of protein is subjected to hydrolysis, then is heat treated to denature the protein. The heat-treated material is then ultrafiltered to eliminate protein.

U.S. Pat. No. 4,402,938 discloses a food and method for making the same from colostrum and milk. In this process, the udder of an ungulate is stimulated with an antigen-like material so that the food factor of the whey is enhanced. The enhanced milk is subsequently ultrafiltered. The retentate is discarded and the permeate is saved. Preservatives are added to the milk/colostrum prior to ultrafiltration.

SUMMARY OF THE INVENTION

A hypoallergenic milk product is provided comprising a permeate substantially free of hyperallergenic protein prepared by filtration of milk or whey through a filtration membrane which will only allow molecules having a molecular weight of less than or equal to about 5 kDa to pass therethrough, the permeate having been prepared without chemical treatment to denature or hydrolyze the protein contained therein prior to filtration. The milk product further includes an added hypoallergenic protein component which may advantageously comprise hypoallergenic protein per se, amino acids, polypeptides having a molecular weight of not more than about 1.5 kDa, or a combination thereof.

The hypoallergenic milk product is prepared by the steps of filtering milk or whey through a filtration membrane. The filtration membrane will only allow molecules with a molecular weight of less than or equal to about 5 kDa to pass therethrough. The permeate is thereafter collected from the filtration step and supplemented with the above-described added hypoallergenic protein component. The permeate may be optionally supplemented with hypoallergenic fat, vitamins and minerals.

It is an object of this invention to produce a new and useful hypoallergenic food product from mammalian milk or whey, and from cow's milk in particular.

It is another object of this invention to obtain the good taste of natural whole or skim milk.

It is an object of the invention to provide a hypoallergenic milk product which retains the nutritional content of natural milk.

It is an object of the invention to provide a hypoallergenic milk product which may serve as a vehicle for delivery of specialized nutritional products.

DETAILED DESCRIPTION OF THE INVENTION

The hypoallergenic milk disclosed hereinafter is formulated upon the fact that protein contained in natural milk is the source of allergens that react with reagins to produce allergic reactions. Similar to the antigen-antibody reaction, it is believed that the allergen molecules in cow's milk, which usually are proteins, have a specific structure which acts as a "key", while the reagins have a corresponding structure which acts as a "lock". While this is the theory upon which the hypoallergenic milk is based, this theory is not meant to be limiting upon the embodiments disclosed hereinafter.

Mammalian milk or whey, such as milk or whey from e.g., cows, sheep or goats, is filtered through an ultrafiltration membrane or filter to remove all hypoallergenic components. The milk is not pretreated by heat denaturation or chemical treatment, e.g., acid or enzyme hydrolysis, prior to ultrafiltration. By "chemical treatment" is meant all forms of treatment of the milk or whey with chemicals other than standard dairy plant rennin treatment directed merely to neutralizing the colloidal particle charge on casein micelles. Such treatment of the milk results in the formation of insoluble casein which may be physically removed, as in the preparation of casein-free sweet whey from whole milk. I have found that such treatments, directed merely to physical removal of casein by centrifugation or filtration, do not adversely affect the taste of the resulting product, unlike chemical treatments such as acid hydrolysis or acid denaturation of protein, and unlike heat denaturation of protein. Casein-free sweet whey may thus be effectively utilized as a substitute for whole or skim milk in the production of my hypoallergenic milk product.

By "milk" as used herein is meant not only whole or skim milk, but any crudely-filtered preparation thereof, such as, but not limited to, whey. By "whole milk" is meant milk as substantially obtained from the animal. By "skim milk" is meant whole milk less all or part of the fat content therein. It therefore may be appreciated that "skim milk" includes such variants as "low fat milk" wherein less than substantially all of the fat content has been removed. By "whey" is meant herein the milk component remaining after all or a substantial portion of the fat and casein contained are removed, or any fraction or variant of whey, such as, for example, sweet whey permeate (i.e., permeate of whey prepared by crude filtration), dried sweet whey, demineralized whey, partially demineralized whey, delactose whey (i.e., whey from which lactose has been removed), whey protein concentrate, and the like.

Sweet whey permeate is particularly useful as a starting material for the practice of the invention. It is a by-product of the cheese manufacturing process. It is typically discarded, used as an animal feed or further processed to obtain lactose. The present invention provides an alternative use for sweet whey permeate.

According to one embodiment, an ultrafiltration membrane is sized to prevent the passage of any substance with a molecular weight greater than 5 kDa. Such excluded substances include, but are not limited to: milk protein; viable or non-viable bacteria; bacterial protein antigen; and milk fat. Alternately, ultrafiltration membranes which prevent the passage of any substance with a molecular weight greater than 1 or 2 kDa may also be used. Ultrafiltration membranes capable of preventing the passage of 1 or 2 kDa molecular weight substances have proportionately smaller pore sizes.

The following milk proteins are trapped by the ultrafiltration membrane (molecular weights are noted in parenthesis): alpha lactalbumin (14 kDa); kappa casein (23 kDa); alpha S-1 casein; alpha S-2 casein; beta casein (24 kDa); beta lactoglobulin (37 kDa); bovine serum albumin (65 kDa); and immunoglobulins (>100 kDa). These milk proteins are considered allergenic. Beta lactoglobulin is a dimer at pH 6.6.

It has been found that decreasing the sizing of the filter decreases the relative amount of three milk proteins—alpha lactalbumin, beta lactoglobulin and bovine serum albumin—remaining in the permeate. Thus, where 0.27, 0.33 and 0.01 units of these proteins, respectively, are found in permeates prepared with a 10 kDa membrane (i.e., a filter membrane which excludes molecules having a molecular weight greater than 10 kDa), permeates prepared with 5 kDa dalton filters contain 0.03, 0.03 and 0.01 units of these same proteins, respectively. A dialysate, prepared using a 3.5 kDa dialysis membrane, contains less than 0.01 units of each of these protein species, resulting in a protein-free dialysate, based upon the limits of the electrophoretic method employed to analyze for protein.

Ultrafiltration membranes having a 3.5 kDa or less molecular weight cut-off are preferred. Polyether sulfone membranes having a 1 kDa or 2 kDa cut-off are available, for example, from Advanced Membrane Technology, San Diego, Calif. and Dow Denmark, Naskov, Denmark, respectively. Ultrafiltration membranes made of ceramic materials may also be used.

Ceramic filters have an advantage over synthetic filters. Ceramic filters can be sterilized with live steam so that the chemical agents, such as chlorine, do not have to be used to sterilize the filter. Synthetic filters, on the other hand, cannot be sterilized with live steam, but instead they must be sterilized with chemical agents, for example, a solution of 200 p.p.m chlorine solution may be used to disinfect the membrane. If a chemical agent is used to disinfect the membrane, the chemical agent may be washed from the filter by flushing the filter with two passes of milk.

A pressure gradient is preferably applied across the ultrafiltration membrane to facilitate filtration. Preferably, the pressure gradient is adjusted to maintain a filter flux of about 24 liters/$m^2$-hour, which is the typical dairy plant filter flux. The filter is advantageously first primed with a small amount of milk and the permeate discarded, prior to beginning filtration. Priming of the filter in this manner is believed to be advantageous to filtering efficiency.

The pH of the milk during filtration should be within the range of about 2 to about 11. The preferred pH is about 6.6. The pH of sweet casein-free whey is typically about 6.1.

The temperature of the milk during ultrafiltration should be within the range of about 40° F. to about 150° F.

Instead of ultrafiltration, the allergenic component of the milk or whey may be removed by dialysis. As is well known, dialysis operates on a principal akin to osmosis. The allergenic protein in the permeate is effectively trapped utilizing a 5 kDa, (preferably a 3.5 kDa, 2 kDa or 1 kDa) ultrafilter or dialysis membrane.

With dialysis, as with ultrafiltration, the permeate that passes through the membrane, i.e. the hypoallergenic component, is saved and utilized. The retentate, i.e., the material which does not pass through the membrane, is discarded or utilized in other commercial applications. A dialysis membrane capable of preventing the passage of materials with a molecular weight of 5 kDa may be used. Other membranes, however, could be used so long as the hyperallergenic component is excluded from the permeate.

The permeate collected from the ultrafiltration process is free of fat, milk protein, bacteria and bacterial protein antigen. The permeate contains, among other things: riboflavin (the substance which gives the permeate a yellow color); lactose (less than 5% by weight); salt or ash containing calcium; $C_7$-$C_{10}$ carbon compounds, particular the seven-carbon compound cis-4-heptanal, which is an unsaturated aldehyde; dimethyl sulfide; and other minerals typically found in pasteurized milk. These materials, as well as milk fat subsequently re-added (after deproteinization), give the enriched permeate the good taste and smell of whole milk. The retentate is of no further use in the hypoallergenic milk manufacturing process, and may be discarded or used in other processes beyond the scope of the invention, for example in the manufacture of ice cream.

The permeate which is deproteinized and defatted may be supplemented with hypoallergenic protein, fat, vitamins, minerals and flavoring so that it meets the minimum daily requirement (M.D.R.) for milk. Preservatives such as phenol, parabens etc. are preferably not added. The permeate may be supplemented, as discussed below, while in liquid form. Alternatively or additionally, it may be freeze dried in any conventional manner, then reconstituted with liquid supplements at a later time.

The supplements include, among other things, a hypoallergenic protein component, hypoallergenic fat, vitamins, minerals and flavoring, such as natural vanilla flavoring. The hypoallergenic protein component may comprise hypoallergenic protein per se, such as protein from cereal or vegetable sources. Alternatively, or additionally, it may comprise free amino acids, or polypeptides of animal source, provided the polypeptides are not larger than about 1.5 kDa, preferably not larger than about 1 kDa.

Sources of hypoallergenic protein include, but are not limited to: oat cereal (which has a high protein level of about 18%); rice cereal; barley cereal; or any other food source having a low allergenicity and ample protein content. Vegetable sources of protein may also be used, so long as they have a low allergenic potential. Vegetable sources of low allergenic protein include, for example, potato and soy isolate. Combinations of the foregoing proteins may also be used.

Oat cereal, for example oatmeal, is preferred because it not only enhances the protein content, it also adds to the taste of the resulting product. The oat cereal is used as a very finely ground flour, to facilitate dissolution into the permeate. About 5 to 10 grams of the very finely ground and sieved cereal flour is added to about 100 cc of permeate. The resulting mixture has a protein content of about 0.9 to 1.8% by weight, which is similar to human breast milk.

When cereals are used, protein soy isolate may also be added to enrich the lysine amino acid value of the cereal. Additionally, the protein may be supplemented with, among other things, methionine, cystine, and iodine to meet the minimum daily requirements (M.D.R.).

Protein soy isolate is preferred for use in hypoallergenic milk which is intended for infants, who require a single source of protein, or children and adolescents with important growth factor requirements. Cereal hypoallergenic protein sources can be used in the hypoallergenic milk for adults. For example, if a multiple source of protein is desired, any combination of hypoallergenic protein sources may be used.

In lieu of, or in addition to, supplementation with hypoallergenic protein, the permeate may be supplemented with amino acids, short chain polypeptides, or a combination of amino acids and short chain polypeptides. By "short chain polypeptide" is meant a polypeptide having a molecular weight of no more than about 1.5 kDa, preferably not more than about 1 kDa. Free amino acids and short chain polypeptides are hypoallergenic regardless of source, and therefore will not contribute to the allergenicity of the milk product. Preferably, the amino acids comprise a mixture of amino acids, most preferably a mixture containing at least the nine amino acids which are essential to the human diet:

| Threonine  | Valine     | Phenylalanine |
| Methionine | Isoleucine | Histidine     |
| Lysine     | Leucine    | Tryptophan    |

The short chain polypeptides may comprise individual polypeptides or a mixture of polypeptides. The short chain polypeptides and amino acids may be obtained by appropriate hydrolysis of any suitable polypeptides or proteins. Preferably, they are obtained from milk proteins, so that the reconstituted hypoallergenic milk product of the invention maintains a portion of the protein nutritional content of whole milk. Hydrolysates of milk proteins are commercially available. For example, a series of hydrolysates are produced by Deltown Chemurgic Corporation, Fraser, N.Y., under the trademark "DELLAC". "DELLAC" CE80PS is a highly hydrolyzed pancreatic digest of casein. "DELLAC" LE80PS is a hydrolyzed pancreatic digest of another milk protein, lactalbumin. High-performance liquid chromatography indicates that these products are free of polypeptides having a molecular weight of greater than about 1.5 kDa. Hydrolysates of non-milk proteins may also be employed, e.g. "DELLAC" SE50M, which is a papaic digest of soy flour.

Each of the aforementioned products may be advantageously utilized in the practice of the invention since they are either free of allergenic milk protein, or are at least free of any milk-derived polypeptides large enough to be considered allergenic.

While it is preferred that the short chain polypeptides and amino acids are added to the permeate after filtration, it is possible that they may be added to the milk or whey prior to filtration. In such cases, it may then be feasible to utilize as a source of short chain polypeptides milk protein hydrolysate which may include some polypeptide species large enough to be considered hyperallergenic, since these larger species will be removed by the filtration step. One example of such a milk protein hydrosylate is "DELLAC" LE80GF, an enzymatic digest of lactalbumin. It consists of 80% by weight protein-derived materials, of which 97 wt.% comprises short chain polypeptide and 3 wt.% whole protein. The product has an average molecular weight to about 2 kDa.

Hydrolysates of lactalbumin are particularly preferred for supplying short chain polypeptides and/or amino acids in the practice of the present invention. Lactalbumin and its hydrolysates contain a relative surplus of the four essential amino acids lysine, methionine, threonine and isoleucine. It can, therefore, be an important supplement to cereal or vegetable protein which is somewhat deficient in these amino acids. Lactalbumin hydrolysates are particularly useful when combined with other protein sources, such as soy isolate or casein hydrolysate, which may be somewhat deficient in the amino acids cystine and methionine.

It should be noted that while the aforementioned refined polypeptide-containing products result from enzyme hydrolysis of single milk proteins, their addition to the permeate prepared according to the present invention does not significantly impact on the taste of the final reconstituted hypoallergenic milk product. This should be contrasted with the situation where whole milk, before filtration, is treated in situ with hydrolytic enzymes. This form of in situ hydrolysis of milk proteins deleteriously impacts on the taste of the resulting product.

The sources of fat (or lipids) may include deproteinized clear butter and butter oil or butter fat, polyunsaturated and mono- and/or polyunsaturated vegetable oil or fat from milk free margarine sources, sesame, safflower, and the like. The foregoing fats are hypoallergenic.

The fat is optionally added to the permeate so that the fat content of the resulting mixture ranges between 0% and about 4% by weight depending upon whether skim, 1%, 2% or 4% homogenized milk is desired. For adults where atherosclerosis prevention is of great importance, the fat source may comprise about ¼ to about ½% deproteinized butter oil and/or about ½ to about 2% low fat polyunsaturated vegetable fat.

Deproteinized hypoallergenic butter for supplementing the permeate may be made from commercially available salt-free, sweet 99.99% anhydrous milk fat. The milk fat is melted in boiling water. The resulting butter oil is then removed from the boiling water, such as by pipetting it off the surface of the water. The process removes, by dilution and washing of the milk fat with water, any protein which may be contained in the fat as a contaminant. The process may be repeated any number of times to ensure the purity of the resulting butter product.

Vitamins and minerals are also optionally added to the protein- and fat-supplemented permeate. Vitamins and minerals are added to the reconstituted, modified hypoallergenic milk so that the milk meets the minimum daily requirement. By way of non-limiting example, the following may be added, based upon one quart of permeate supplemented with hypoallergenic protein and fat: 400 micrograms of water dispersible Vitamin D; 2100 micrograms of water-dispersible Vitamin A; 60 milligrams of Vitamin C acetate; folic acid; calcium pantothenate; biotin; pyridoxine; minerals such as calcium triphosphate, iron as ferrous sulfate, and zinc as zinc sulfate. The foregoing are exemplary of the vitamins and minerals that may be added to the hypoallergenic milk. Of course, other vitamins and minerals which are known to those of ordinary skill in the art may also be added.

Additives to enhance the flavor and consistency of the hypoallergenic milk may also be added. Exemplary additives include: hypoallergenic bean gum derived from guar gum (3 to 4 pounds per 1,000 gals. of hypoallergenic milk); carrageenan; and/or lecithin of hypoallergenic vegetable bean source, such as soy bean (20 lbs/1000 gallons of hypoallergenic milk). Each of these additives impart a creamy consistency (acts as an emulsifier) to the hypoallergenic milk. Natural vanilla may also be added to enhance the flavor of hypoallergenic milk.

After the hypoallergenic protein component and optional fats, vitamins, minerals and additives to enhance flavor and consistency have been added to the permeate, the hypoallergenic milk is preferably blended in an emulsifying and diffusing apparatus operating at between about 2,500 and about 3,500 r.p.m., to ensure thorough mixing. The blended hypoallergenic milk is then homogenized at a pressure ranging from about 2,000 to about 4,000 P.S.I., pasteurized at about 170° F. for about 30 minutes, and then flashed sterilized at about 290° F. for about 12 seconds and packaged into aseptic containers. Such containers are made of materials which will not leach into the packaged product. The materials include, but are not limited to, glass, waxed cardboard or metal. Alternatively, the permeate may be pasteurized before the various supplements have been added.

The meticulous removal of substantially all allergenic protein by an ultrafilter or dialysis membrane has superior advantage regarding hypoallergenicity. The permeate is deproteinized as evidenced by the absence of protein bands upon SDS-PAGE, sensitive to the application of 30 nanograms/microliter or greater concentration of protein. Thus, it is understood that as used herein, the expression "substantially completely deproteinized" or "substantially free of milk protein" in referring to a milk preparation, means a preparation free of protein bands upon SDS-PAGE sensitive to the presence of protein concentrations of 30 nanograms/microliter or higher.

Lactase enzyme may be added to the hypoallergenic milk for use by an older child or adult where lactose intolerance may be a consideration.

The hypoallergenic milk may be substituted for milk in any formulation in which milk is used. For example, hypoallergenic milk may be used as a beverage or in beverages, or solid food products such as candy, milk chocolate, cookies, cakes, breakfast cereals and the like. The hypoallergenic milk product may also be utilized as a vehicle for the delivery of specialized nutritional products, which might otherwise have an objectionable taste to the patient. Thus, use of the hypoallergenic milk product as a vehicle for offensive-tasting enteral products may obviate the need for introducing such products by stomach tube, which occurs in patients suffering from such diseases as ileitis, colitis, and geriatric nursing home patients.

One non-limiting hypoallergenic milk product according to the present invention suitable for infants contains the following components, based upon 100 ml of product. The amount of each component may be adjusted according to need.

| Protein | |
| --- | --- |
| Soy protein isolate | 1.8 g |
| Oatmeal protein (optional) | 0.9 to 1.8 g |

| -continued | |
|---|---|
| Fat | 3.7 g |
| Carbohydrate | |
| Lactose | 4.6 g |
| Minerals | |
| Sodium | 41 to 49 mg |
| Potassium | 140 to 152 mg |
| Calcium | 110 to 119 mg |
| Phosphorus | 89 to 93 mg |
| Chloride | 63 to 65 mg |
| Iron (fortified) | 0.05 to 1.2 mg |
| Zinc | 0.38 to 0.43 mg |
| Iodine | 10 micrograms |
| Amino Acids | |
| Methionine | 10 micrograms |
| Cystine | 10 micrograms |
| Vitamins | |
| Vitamin A (water dispersible) | 210 International Units ("I.U.") |
| Vitamin C (as acetate) | 6.0 mg |
| Vitamin D (water dispersible) | 42 I.U. |
| Vitamin E | 1.0 mg |
| Thiamine | 0.04 mg |
| Riboflavin | 0.14 to 0.16 mg |
| Niacin | 0.08 mg |
| Pyridoxine | 0.04 to 0.05 mg |
| Vitamin $B_{12}$ | 0.32 micrograms |
| Folic Acid | 5.0 micrograms |

According to another embodiment, a hypoallergenic milk product suitable for infants has the foregoing components, except that the soy protein isolate, methione and cystine are omitted in favor of a mixture of free amino acids, comprising preferably at least all the essential amino acids, or, alternatively a mixture of short chain polypeptides. Preferably, the infant formula utilizes a mixture of short chain polypeptides derived from milk protein, such as any of the available hydrolysates of milk proteins described above.

The method of the invention is effective in reducing the protein content of milk from 3.6% to 0.26%, a reduction of more than 90%. It should be noted that by utilizing a filter capable of retaining 5 kDa molecular weight species, 90% more protein is removed from the permeate than with a 10 kDa filter. A filter capable of retaining 3.5 kDa molecular weight species results in the complete absence of protein, as evidenced by SDS-PAGE.

The treatment of the invention effectively removes all casein, and all the other milk proteins, and all immunoglobulins. The trace amounts of the other proteins remaining in the permeate are heat denatured by the pasteurization process utilized above.

The invention will now be described in more detail with reference to the following specific, non-limiting examples:

EXAMPLE 1

Whole cow's milk was passed through an ultrafiltration membrane ("A.E.S.-1", Advanced Membrane Technology, San Diego, Calif.) having a 1 kDa molecular weight cut-off at 40° F. and pH 6.6. Filtration was facilitated by applying a pressure gradient of about 5 psi across the membrane. The absence of protein in the permeate was demonstrated by the absence of protein bands upon sodium dodecyl sulfate polyacrylamide gel electrophoresis ("SDS-PAGE") and silver staining. The use of a silver stain is generally three times more sensitive for detection of proteins than colored stains such as Koomasie Blue. Nine ml of the permeate was then supplemented with 203.8 mg "DELLAC" LE80PS (Deltown Chemurgic Corp.), which comprises 80% by weight amino acids and oligopeptides from pancreatic digestion of lactalbumin. "DELLAC" LE80PS has been determined to be non-allergenic by a guinea pig challenge test. The supplemented permeate was transferred to a 10 ml screw top test tube and further processed for 20 minutes by mixing and shaking to produce a homogeneous solution.

EXAMPLE 2

Nine ml of the permeate prepared according to Example 1 was supplemented with 301 mg of "DELLAC" CE80GPS, which comprises 80% by weight of amino acids and oligopeptides resulting from hydrolysis of casein by aminopeptidases extracted from *Streptococcus lactis*. "DELLAC" CE80GPS has been determined to be non-allergenic by a guinea pig challenge test. The supplemented permeate was then transferred to a 10 ml screw top test tube and further processed for 20 minutes by mixing and shaking to produce a homogeneous solution.

EXAMPLE 3

9 ml of the permeate prepared according to Example 1 was supplemented with 200 mg of "DELLAC" CE80PS, comprising 80% by weight of amino acids and oligopeptides resulting from the pancreatic digest of casein. It has been determined to be non-allergenic by a guinea pig challenge test. This sample was transferred to a 10 ml screw top test tube and further processed for 20 minutes by mixing and shaking to produce a homogeneous solution.

EXAMPLE 4

Nine ml of the permeate prepared according to Example 1 was supplemented with 302.1 mg of "DELLAC" SE50M, a papiac digest of soy flour comprising 50% by weight amino acids and oligopeptides. This sample was transferred to a 10 ml screw top test tube and further processed for 20 minutes by mixing and shaking to produce a homogeneous solution.

EXAMPLE 5

To the supplemented permeate of Example 2 there was further added 0.1 ml of cleared anhydrous butter oil (prepared according to Example 11, below). This sample was transferred to a 10 ml screw top test tube and further processed for 20 minutes by mixing and shaking to produce a homogeneous solution. The absence of protein was demonstrated by SDS-PAGE.

EXAMPLE 6

To the supplemented permeate prepared according to Example 4 there was added 0.1 ml of cleared anhydrous butter oil (prepared according to Example 11, below). This sample was transferred to a 10 ml screw top test tube and further processed for 20 minutes by mixing and shaking to produce a homogeneous solution.

EXAMPLE 7

Sweet casein-free whey derived from whole cow's milk was passed through a 1 kDa cut-off ultrafiltration membrane ("A.E.S.-1", Advanced Membrane Technology, San Diego, Calif.). The milk was maintained at a temperature of 5°–10° C. and a pH of 6.1. Filtration was facilitated by applying a pressure gradient of about 60–80 psi across the membrane. The absence of protein in the permeate was confirmed by SDS-PAGE. 250 ml of the permeate was then enriched with 3126 ml of "DELLAC" LE80PS. The sample was processed by shaking and mixing for 20 minutes to produce a homogeneous mixture.

EXAMPLE 8

125 ml of the enriched permeate of Example 7 was supplemented by adding 7.5 grams of a very finely ground and sifted oat soy flour, in the form of commercially available oat soy powder, with constant stirring for 20 minutes. The oat flour-enriched permeate was then pasteurized for 20 seconds with constant stirring in a double boiler at 72° C. (170° F.), and then further supplemented with 1.25 ml of cleared hypoallergenic anhydrous butter oil (prepared as in Example 11, below). The resulting reconstituted hypoallergenic milk product was decanted into a 4 ounce sterile glass bottle and refrigerated. It was chilled, then homogenized using a homogenizer operating at 9000 rpm, and then chilled again. The good smell and taste of cow's milk was observed, with an appearance similar to skim milk.

EXAMPLE 9

Examples 7 and 8 were repeated, substituting skim milk for sweet casein-free whey. The pH at which the milk was maintained during filtration was increased to 6.6. The resulting hypoallergenic milk product displayed the good smell and taste of cow's milk, with an appearance similar to conventional skim milk.

EXAMPLE 10

Fresh whole guernsey cow's milk was collected (7:30 a.m.) and separated (9:30 a.m.) from fat. The skim milk was then brought to 104° F. (40° C.) temperature for separation. The skim milk was then placed in an ice bath to a temperature of 52° F. Fourteen liters of this milk was transferred to a cold room (50° F.). Fourteen liters of this milk was transferred to a cold room (50° F.) and was subjected to constant stirring. The skim milk was placed in six 90 ml, 3,500 molecular weight dialysis tubes tied at each end (i.e., species > 3.5 kDa do not pass through) and dialyzed against deionized, distilled water. The dialysate, which contained 6.1% solids, on chemical analysis revealed 0.27% protein or polypeptides, and other nitrogen-containing compounds by the BCA method, *Clinical Chemistry* 32:120 (1986). Gel electrophoresis of the dialysate, which is sensitive to the application of 30 ng/microliter protein to the gel, revealed no protein. It is significant to note that neither casein, nor any of the other milk proteins, were present in the permeate, as established by gel electrophoresis.

Two hundred and forty ml of this dialysate was then mixed with 25 grams of an enriched soy solids powder containing hypoallergenic soy oil, lecithin as an emulsifier, and vitamins and minerals.

The addition of the soy powder resulted in a hypoallergenic milk formulation containing about 2% protein (weight/volume) and about 2% fat (weight/volume). Constant stirring for 20 minutes resulted in a colloidal suspension.

The suspension was then pasteurized at 170° F. for 30 minutes in a double boiler with further constant stirring. This heating in a double boiler also serves to heat denature any remote trace of protein. The milk was then poured into four 8 ounce sterile glass bottles and refrigerated. The tan colored colloidal suspension was found to be maintained upon gross inspection at two hours, eight hours, and eighteen hours after preparation.

EXAMPLE 11

A. a hypoallergenic butter product substantially completely free of hyperallergenic protein may be prepared as follows:

Twenty grams of anhydrous milk fat 99.99% pure (0.01 moisture) is cleared of any possible trace of protein in 5,000 ml of boiling water, rendering a hypoallergenic butter oil. The butter oil is then pipetted off the water.

B. 0.1 cc of the butter oil was added to 9 ml of the permeate prepared according to Example 1. The absence of protein bands was observed upon subjecting the product to SDS-PAGE.

EXAMPLE 12

Skim milk was first enriched by adding a sufficient quantity of "DELLAC" LE80GF to product 1.5 wt.% concentration of LE80GF prior to ultrafiltration. The enriched milk was passed through an ultrafiltration membrane ("A.E.S.-1", Advanced Membrane Technology, San Diego, Calif.), having a 1 kDa molecular weight cut-off. The milk was maintained at 70° F. and pH 6.6. Filtration was facilitated by applying a pressure gradient of about 350 p.s.i. across the membrane, to obtain a filter flux equal to or in excess of 24 liters per square meter of ultrafiltration membrane, per hour. The formulation was then transferred to screw top containers, and refrigerated.

EXAMPLE 13

Example 12 was repeated substituting an ultrafiltration membrane having a 2 kDa molecular weight cut-off ("GR90 2K", Dow Denmark, Naskov, Denmark), for the 1 kDA cut-off ultrafiltration membrane used in Example 12.

EXAMPLE 14

Example 12 was repeated substituting casein-free sweet whey for skim milk and decreasing the pH to 6.1 from 6.6. The pressure gradient was decreased from 350 p.s.i. to 75 p.s.i. to obtain a filtration flux of 24 l/$m^2$-hour. The permeate was then transferred to screw top containers.

EXAMPLE 15

Example 15 was repeated, substituting a 2 kDa cut off membrane ("GR90 2K", Dow Denmark, Naskov, Denmark) for the 1 kDa cut-off filter used in Example 15. The pressure gradient was increased to 350 p.s.i. to achieve a dairy plant filtration flux rate of 24 liters/$m^2$-hour.

EXAMPLE 16

A crude permeate of casein-free sweet whey was prepared by passing casein-free sweet whey through an ultrafiltration membrane ("HFK 131" polyether sulfone 10K, Koch Membrane System, Inc., Wilmington, Mass.), having a 10K Da molecular weight cut off. The casein-free sweet whey was maintained at 70° F. and pH 6.1 Filtration was facilitated by applying a pressure gradient of about 40–45 p.s.i. across the membrane. The crude permeate was enriched by adding a sufficient quantity of "DELLAC" LE80GF to produce a 1.5 wt.% concentration of LE80GF. The enriched crude permeate was further purified by passage through a 1 kDa cut-off ultrafiltration membrane ("A.E.S.-1", Advanced Membrane Technology, San Diego, Calif.) at 70° F. and pH 6.1. Filtration was facilitated by maintaining a pressure gradient of about 75 p.s.i. to provide a filter flux of 24 1/m²-hour. The final ultrafiltered permeate was then transferred to screw top containers.

EXAMPLE 17

Example 16 was repeated substituting the 2 kDa cut-off ultrafiltration membrane ("GR90 2K", Dow Denmark, Naskov, Denmark) for the 1 kDa cut-off ultrafiltration used in Example 16. The pressure gradient required was increased to 350 p.s.i. The permeate was then transferred to screw top containers.

EXAMPLE 18

500 ml of the final ultrafiltered permeate of Example 16 was pasteurized at 72° C. for 20 minutes. This heating further serves to denature any remaining trace of protein. The permeate was then supplemented as follows: 15 grams of finely ground and sifted oat soy powder in the form of commercially available oat soy powder were added to the pasteurized permeate, followed by the addition of 2.5 ml of cleared anhydrous butter oil (as prepared in Example 11). The enriched permeate was then homogenized using a homogenizer operating at 9000 RPM. The formulation was then decanted into two 4 ounce glass bottles and refrigerated. The resulting tan colored suspension was found to be maintained upon gross inspection at two, eight and eighteen hours following preparation. The good taste and smell of cow's milk was observed, with an appearance similar to skim milk.

The presence of medication utilized to treat milk-producing cows is undesirable in milk for human consumption. The ultra filtration method described herein is believed to effectively reduce the level of veterinary pharmaceuticals contained in cow's milk. Approximately 75% of monocyclic drugs, e.g., penicillin and sulfonamides, which may be present in the milk, are attached to the milk's protein fraction. Approximately 25% or more of tricyclic compounds, and approximately 50% of bicyclic compounds, are similarly found attached to the protein fraction. Thus, it may be readily appreciated that removal of milk protein, as in the practice of the present invention, serves also to substantially reduce the level of veterinary medications which may be contained in cow's milk.

The present invention may be embodied in other specific forms without departing from the spirit or essential attributes thereof and, accordingly, reference should be made to the appended claims, rather than to the foregoing specification, as indicating the scope of the invention.

I claim:
1. A hypoallergenic milk product comprising:
   (a) a permeate of milk substantially free of hyperallergenic protein prepared by filtration of milk through a filtration membrane which will only allow molecules with a molecular weight of less than or equal to about 5 kDa to pass therethrough, said permeate having been prepared without chemical treatment to denature or hydrolyze the protein contained therein prior to filtration; and
   (b) added amino acids, added polypeptides having a molecular weight of not more than about 1.5 kDa, or a combination thereof.

2. A milk product according to claim 1 further comprising hypoallergenic fat.
3. A milk product according to claim 1 wherein the added amino acids or polypeptides are derived from a milk protein.
4. A milk product according to claim 3 wherein the added amino acids or polypeptides are derived from lactalbumin.
5. A milk product according to claim 1 wherein the added polypeptides have a molecular weight of not more than about 1 kDa.
6. A milk product according to claim 1 wherein the milk subject to filtration comprises skim milk.
7. A milk product according to claim 1 wherein the milk subject to filtration comprises cow's milk.
8. A milk product according to claim 1 wherein said permeate is free of molecules having a molecular weight greater than about 3.5 kDa.
9. A milk product according to claim 8 wherein said permeate is free of molecules having a molecular weight greater than about 2 kDa.
10. A milk product according to claim 9 wherein said permeate is free of molecules having a molecular weight greater than about 1 kDa.
11. A milk product according to claim 1 further containing hypoallergenic protein.
12. A milk product according to claim 11 wherein the hypoallergenic protein is selected from the group consisting of cereal protein, vegetable protein, and combinations thereof.
13. A milk product according to claim 2 wherein the hypoallergenic fat is selected from the group consisting of deproteinized butter, vegetable oil, and combinations thereof.
14. A hypoallergenic milk product comprising:
   (a) a whey permeate substantially free of hyperallergenic protein prepared by filtration of whey through a filtration membrane which will only allow molecules with a molecular weight of less than or equal to about 5 kDa to pass therethrough, said permeate having been prepared without chemical treatment to denature or hydrolyze the protein contained therein prior to filtration; and
   (b) an added hypoallergenic protein component selected from the group consisting of hypoallergenic protein, amino acids, polypeptides having a molecular weight of not more than about 1.5 kDa, or a combination thereof.
15. A milk product according to claim 14 further comprising hypoallergenic fat.
16. A milk product according to claim 14 wherein the added protein component comprises amino acids and polypeptides derived from a milk protein.
17. A milk protein according to claim 14 wherein the polypeptides have a molecular weight of not more than about 1 kDa.
18. A milk product according to claim 14 wherein the amino acids and polypeptides are derived from lactalbumin.
19. A milk product according to claim 14 wherein the whey permeate is free of molecules having a molecular weight of greater than about 3.5 kDa.
20. A milk product according to claim 19 wherein the whey permeate is free of molecules having a molecular weight of greater than about 2 kDa.
21. A milk product according to claim 20 wherein the whey permeate is free of molecules having a molecular weight of greater than about 1 kDa.

22. A milk product according to claim 14 containing hypoallergenic protein selected from the group consisting of cereal protein, vegetable protein, and combinations thereof.

23. A milk product according to claim 15 wherein the hypoallergenic fat is selected from the group consisting of deproteinized butter, vegetable oil, and combinations thereof.

24. A process of making a hypoallergenic milk product comprising the steps of:
 (a) filtering milk through a filtration membrane in the absence of chemical treatment to denature or hydrolyze the protein contained therein, which filtration membrane will only allow molecules with a molecular weight less than or equal to about 5 kDa to pass therethrough;
 (b) collecting the permeate from the filtration step; and
 (c) supplementing the permeate with amino acids, polypeptides having a molecular weight of not more than about 1.5 kDa, or a combination thereof.

25. A process according to claim 24 comprising the further step of supplementing the permeate with hypoallergenic fat.

26. A process according to claim 24 wherein the supplementing amino acids or polypeptides are derived from a milk protein.

27. A process according to claim 26 wherein the supplementing amino acids or polypeptides are derived from lactalbumin.

28. A process according to claim 24 wherein the supplementing polypeptides have a molecular weight of not more than about 1 kDa.

29. A process according to claim 24 wherein the milk subject to filtration comprises cow's milk.

30. A process according to claim 24 wherein the filter membrane will only allow molecules with a molecular weight of less than or equal to about 3.5 kDa to pass therethrough.

31. A process according to claim 30 wherein the filter membrane will only allow molecules with a molecular weight of less than or equal to about 2 kDa to pass therethrough.

32. A process according to claim 31 wherein the filter membrane will only allow molecules with a molecular weight of less than or equal to about 1 kDa to pass therethrough.

33. A process according to claim 24 wherein the filtering is by dialysis.

34. A process of making a hypoallergenic milk product comprising the steps of:
 (a) filtering whey through a filtration membrane in the absence of chemical treatment to denature or hydrolyze the protein contained therein, which filtration membrane will only allow molecules with a molecular weight less than or equal to about 5 kDa to pass therethrough;
 (b) collecting the permeate from the filtration step; and
 (c) supplementing the permeate with an added hypoallergenic protein component selected from the group consisting of hypoallergenic protein, amino acids, polypeptides having a molecular weight of not more than about 1.5 kDa, or a combination thereof.

35. A process according to claim 34 comprising the further step of supplementing the permeate with hypoallergenic fat.

36. A process according to claim 34 wherein the supplementing amino acids or polypeptides are derived from a milk protein.

37. A process according to claim 34 wherein the supplementing polypeptides have a molecular weight of not more than about 1 kDa.

38. A process according to claim 36 wherein the milk protein comprises lactalbumin.

39. A process according to claim 34 wherein the filtration membrane will only allow molecules with a molecular weight of less than or equal to about 3.5 kDa to pass therethrough.

40. A process according to claim 39 wherein the filtration membrane will only allow molecules with a molecular weight of less than or equal to about 2 kDa to pass therethrough.

41. A process according to claim 40 wherein the filtration membrane will only allow molecules with a molecular weight of less than or equal to about 1 kDa to pass therethrough.

42. A process according to claim 34 wherein the filtering is by dialysis.

43. A process according to claim 34 containing hypoallergenic protein selected from the group consisting of cereal protein, vegetable protein, and combinations thereof.

44. A milk product according to claim 35 wherein the hypoallergenic fat is selected from the group consisting of deproteinized butter, vegetable oil, and combinations thereof.

45. A hypoallergenic milk product comprising:
 (a) a permeate substance free of hypoallegenic protein containing molecules therein having a molecular weight of about 5 kDa or less, said permeate being selected from the group consisting of milk permeate and whey permeate; and
 (b) at least 1% by weight of an additive selected from the group consisting of hypoallergenic protein, short chain polypeptides, amino acids and mixtures thereof.

46. A milk product according to claim 45 further including hypoallergenic fat.

47. A milk product according to claim 46, wherein said hypoallergenic fat is selected from the group consisting of deproteinized butter, vegetable oil and combinations thereof.

48. A process for making a hypoallergenic milk product comprising:
 (a) separating milk or whey to isolate molecules having a molecular weight of about 5 kDa or less to product a permeate;
 (b) collecting said permeate; and
 (c) admixing an additive selected from the group consisting of hypoallergenic protein, amino acids, short chain polypeptides and mixtures thereof.

49. A process according to claim 48 further comprising adding hypoallergenic fat to said permeate.

50. A process according to claim 49 wherein said hypoallergenic fat is selected from the group consisting of deproteinized butter, vegetable oil and combinations thereof.

* * * * *